US012636201B2

(12) United States Patent
Sharma et al.

(10) Patent No.: US 12,636,201 B2
(45) Date of Patent: May 26, 2026

(54) MEDICAL DEVICES, SYSTEMS, AND RELATED METHODS

(71) Applicants: Boston Scientific Scimed, Inc., Maple Grove, MN (US); Boston Scientific Medical Device Limited, Galway (IE)

(72) Inventors: Deepak Kumar Sharma, Muzaffarnagar (IN); Sharath Kumar G, Kanakapura (IN); Paul Smith, Smithfield, RI (US); Barry Weitzner, Acton, MA (US)

(73) Assignees: Boston Scientific Scimed, Inc., Maple Grove, MN (US); Boston Scientific Medical Device Limited, Galway (IE)

( * ) Notice: Subject to any disclaimer, the term of this patent is extended or adjusted under 35 U.S.C. 154(b) by 241 days.

(21) Appl. No.: 18/403,959

(22) Filed: Jan. 4, 2024

(65) Prior Publication Data

US 2024/0216185 A1     Jul. 4, 2024

Related U.S. Application Data

(60) Provisional application No. 63/478,434, filed on Jan. 4, 2023.

(51) Int. Cl.
| | |
|---|---|
| *A61F 13/26* | (2006.01) |
| *A61B 1/00* | (2006.01) |
| *A61B 1/018* | (2006.01) |
| *A61B 1/273* | (2006.01) |
| *A61F 13/20* | (2006.01) |

(52) U.S. Cl.
CPC ........ *A61F 13/266* (2013.01); *A61B 1/00133* (2013.01); *A61B 1/018* (2013.01); *A61B 1/2736* (2013.01); *A61F 13/2074* (2013.01); *A61F 2013/2014* (2013.01)

(58) Field of Classification Search
CPC ........ A61F 13/26; A61F 13/20; A61F 13/266; A61B 1/00; A61B 1/018; A61B 1/273; A61B 1/0011; A61B 1/00137; A61B 17/0057; A61B 2017/00818; A61B 2017/00296; A61B 2017/00597
See application file for complete search history.

(56) References Cited

U.S. PATENT DOCUMENTS

| | | | |
|---|---|---|---|
| 2007/0135826 A1* | 6/2007 | Zaver ............... | A61B 17/12022 606/157 |
| 2021/0361342 A1* | 11/2021 | Sharma ................... | A61M 1/87 |

* cited by examiner

*Primary Examiner* — Vi X Nguyen
(74) *Attorney, Agent, or Firm* — Bookoff McAndrews PLLC

(57) ABSTRACT

A medical device may comprise a handle, wherein the handle includes a movable body and a main body; a cap configured to be coupled to a distal end of a scope; a patch, wherein the patch is moveable relative to the cap; and a petal body. The patch may be removably coupled to the petal body. The medical device may further comprise an actuator body coupling the patch to the moveable body such that movement of the moveable body extends the patch from the cap. The petal body may be configured to transition between a closed configuration in which the patch is retracted, and an open configuration in which the patch is extended radially-outward from a central longitudinal axis of the scope.

15 Claims, 7 Drawing Sheets

MEDICAL DEVICES, SYSTEMS, AND RELATED METHODS

CROSS-REFERENCE TO RELATED APPLICATIONS

This application claims the benefit of priority of U.S. Provisional Patent Application No. 63/478,434, filed on Jan. 4, 2023, the entirety of which is incorporated herein by reference.

TECHNICAL FIELD

Various aspects of the present disclosure relate generally to systems, devices, and methods for delivering patches. More specifically, aspects of the disclosure pertain to systems, devices, and/or methods for delivering patches, for example, for hemostasis, via medical devices, such as endoscopes.

BACKGROUND

Bleeding ulcers, for example, in a subject's gastrointestinal (GI) tract, are often difficult to manage and/or provide hemostasis. For example, common treatments for bleeding ulcers include injection therapies, thermal therapies, mechanical therapies, and hemostatic powders. Such therapies are often expensive and/or time-consuming. Furthermore, such therapies may not be able to treat a larger surface area, for example, a larger ulcer in the GI tract. Additionally, a common treatment for chronic ulcers is a gastric bypass. Such procedures may be more difficult, more time-consuming, more costly, and/or less effective/accurate than a minimally-invasive procedure to position a patch on one or more ulcers. Therefore, a need exists for systems, devices, and/or methods for positioning and/or deploying one or more hemostatic patches with one or more portions of a subject.

SUMMARY

Aspects of this disclosure include medical systems and devices comprising a biocompatible patch and methods of use thereof, e.g., methods of delivering a patch to a target site of a patient, for example, to help heal an ulcer and/or to perform hemostasis. Each of the aspects disclosed herein may include one or more of the features described in connection with any of the other disclosed aspects.

According to one aspect, a medical device may comprise a handle, wherein the handle includes a movable body and a main body; a cap configured to be coupled to a distal end of a scope; a patch, wherein the patch is moveable relative to the cap; and a petal body. The patch may be removably coupled to the petal body. The medical device may further comprise an actuator body coupling the patch to the moveable body such that movement of the moveable body extends the patch from the cap. The petal body may be configured to transition between a closed configuration in which the patch is retracted, and an open configuration in which the patch is extended radially-outward from a central longitudinal axis of the scope.

In other aspects, the medical device may include one or more of the following features. The petal body may be a plurality of petal bodies, and the patch may be removably coupled to each of the plurality of petal bodies. The cap may include a ridge configured to couple to the patch. The petal body may be coupled to the cap via a hinge assembly. The petal body may be configured to pivot relative to the cap when the moveable body is translated proximally. The actuator body may include a plurality of control bodies, and each of the control bodies may be coupled to a separate petal body. The petal body may include a slot at a distal portion of the petal body, and the slot may receive a portion of the patch. The patch may include a plurality of adhesion members positioned about at least a portion of a perimeter of the patch. The hinge assembly may be configured to bias the petal body towards the closed configuration. The actuator body may extend through the main body and may be coupled to the moveable body. The cap may include a protrusion extending circumferentially about the cap. The movable body of the handle may be movable within a slot in the main body of the handle. Each of the plurality of petal bodies may be positioned circumferentially about a distal portion of the cap. Each of the control bodies may be coupled together at a joint proximal to the cap and extend distally from the joint, and the actuator body may further includes a first actuator body extending proximally from the joint. The patch may include a hemostatic agent.

In other aspects, a medical system may comprise an endoscope, including a distal end including one or more imaging devices; and a medical device. The medical device may include a handle, wherein the handle includes a movable body and a main body; a cap configured to be coupled to a radial exterior of the distal end of the endoscope; a patch, wherein the patch is movable relative to the cap; and a petal body, wherein the patch is removably coupled to the petal body. The petal body may be configured to transition between a closed configuration in which the patch is retracted, and an open configuration in which the patch is extended radially-outward from a central longitudinal axis of the endoscope. Movement of the movable body may be configured to pivot the petal body and at least partially deploy the patch.

In other aspects, the medical device may include one or more of the following features. An actuator body configured to urge the petal body proximally when the movable body is moved proximally. The handle may include a marker configured to indicate a position of the moveable body relative to the main body at which the patch is released from the cap.

In other aspects, a medical device may comprise an actuator body including a plurality of control bodies; a cap configured to be coupled to a distal end of a second medical device, wherein the cap includes a plurality of petal bodies; and a patch, wherein the patch is removably coupled to each of the plurality of petal bodies. Each of the petal bodies may be coupled to a separate control body of the plurality of control bodies such that proximal movement of the actuator body pivots each of the plurality of petal bodies via the plurality of control bodies, and the patch may be coupled to a distal portion of each of the petal bodies such that movement of the actuator body at least partially deploys the patch. In some examples, each of the petal bodies may include a slot at a distal end portion of the petal body, and a respective portion of the patch may be movably positioned within each of the slots of the plurality of petal bodies.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

DETAILED DESCRIPTION

Reference will now be made in detail to aspects of the present disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. Throughout the figures included in this application, arrows labeled "P" and "D" are used to show the proximal and distal directions in the figure. As used herein, the terms "comprises," "comprising," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." Further, relative terms such as, for example, "about," "substantially," "approximately," etc., are used to indicate a possible variation of ±10% in a stated numeric value or range.

Embodiments of this disclosure seek to improve a physician's ability to position and/or deploy a patch within a patient's body during a medical procedure, help reduce the need to remove and reintroduce an endoscope or other medical device into the patient's body, help perform hemostasis within the patient, and reduce overall procedure time, among other aspects.

Figure 1:
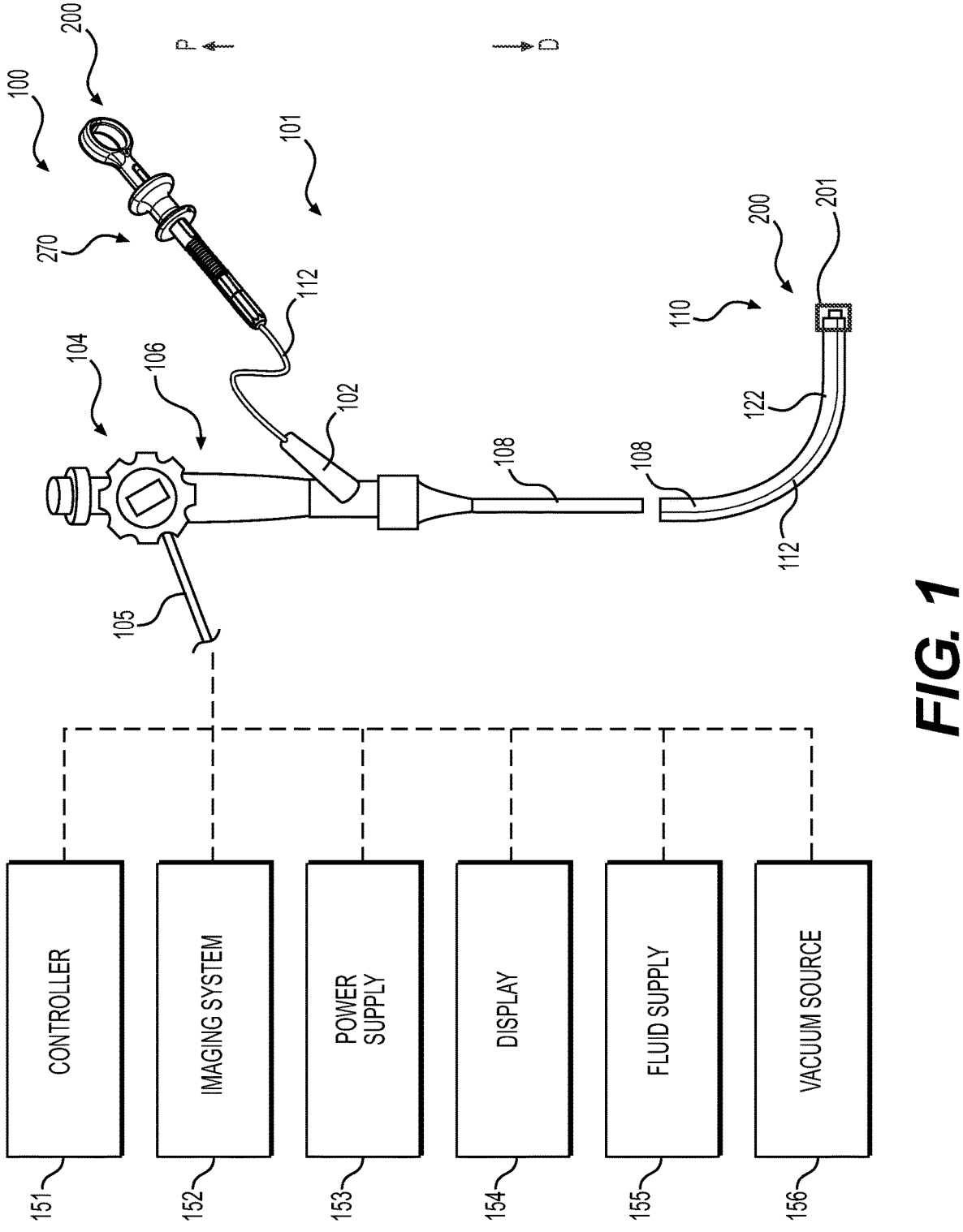
FIG. 1 is a perspective view of an exemplary medical system, including an exemplary medical device and an endoscope, according to aspects of this disclosure.

FIG. 1 shows a perspective view of a medical system 100. Medical system 100 may include an endoscope 101 and a medical device 200. Endoscope 101 may include a handle assembly 106 and a flexible tubular shaft 108 ("shaft 108").

As discussed in detail herein, medical device 200 may include or otherwise be coupled to a patch delivery system, for example, to position and/or deliver a patch 250 (FIG. 2) to one or more portions of tissue within a subject, which may help perform hemostasis within the subject. Moreover, medical device 200 may be coupled to one or more portions of endoscope 101, for example, in order to deliver one or more portions of medical device 200 to a treatment site.

Handle assembly 106 may include a biopsy port 102, one or more actuators 104, and an umbilicus 105. Umbilicus 105 may extend from handle assembly 106 to one or more auxiliary devices. The flexibility of shaft 108 may be sufficient to allow shaft 108 to bend, to facilitate navigation of shaft 108 through a subject's tortuous anatomical passages. Shaft 108 may terminate at a distal tip 110. Shaft 108 may include an articulation section 122 for deflecting distal tip 110 in up, down, left, and/or right directions. FIG. 1 illustrates shaft 108 as two separate components for illustration purposes only, and shaft 108 may extend from handle assembly 106 to distal tip 110, and may be any suitable length. In one example, articulation section 122 may provide for full retroflexion (e.g., rotation of distal tip 110 through an arc of 180 degrees) or only partial retroflexion (e.g., rotation of distal tip 110 through an arc of less than 180 degrees). Endoscope 101 also may include one or more lumens extending therethrough, and one or more openings in communication with the one or more lumens (such as an opening at a distal end face of endoscope 101). For example, the one or more lumens may extend through handle assembly 106 and shaft 108, and the one or more openings may be on handle assembly 106 and distal tip 110.

As mentioned, one or more auxiliary devices may be operatively coupled to endoscope 101. Exemplary auxiliary devices may include a controller 151, an imaging system 152, a power supply 153, a display 154, a fluid supply 155, and/or a vacuum source 156, each of which is briefly described below. Controller 151 may include, for example, any electronic device capable of receiving, storing, processing, generating, and/or transmitting data according to instructions given by one or more programs. Controller 151 may be operatively coupled to, or be part of, one or more of endoscope 101 and the other auxiliary devices, to control one or more aspects of their operation.

Power supply 153 may include any suitable power source, and associated connectors (e.g., electrically-conductive wires), for supplying electronic components in the auxiliary devices and endoscope 101 with electrical power. Fluid supply assembly 155 may include a reservoir, a medical irrigation bag, a pump, and any suitable connectors (e.g., tubing for fluidly coupling fluid supply 155 and endoscope 101). The pump may supply a flow of pressurized fluid to one or more of the lumens in endoscope 101, and the pressurized fluid flow may be emitted from distal tip 110. Vacuum source 156 may provide suction or vacuum pressure to one or more lumens of the endoscope or other devices, and thereby provide a suction force to draw material toward and/or into endoscope 101 or another device. Although illustrated as separate components, it is understood that all or any combination, or elements of, controller 151, imaging system 152, power supply 153, display 154, fluid supply 155, and/or vacuum source 156 may be integrated in a single unit.

Figure 4A:
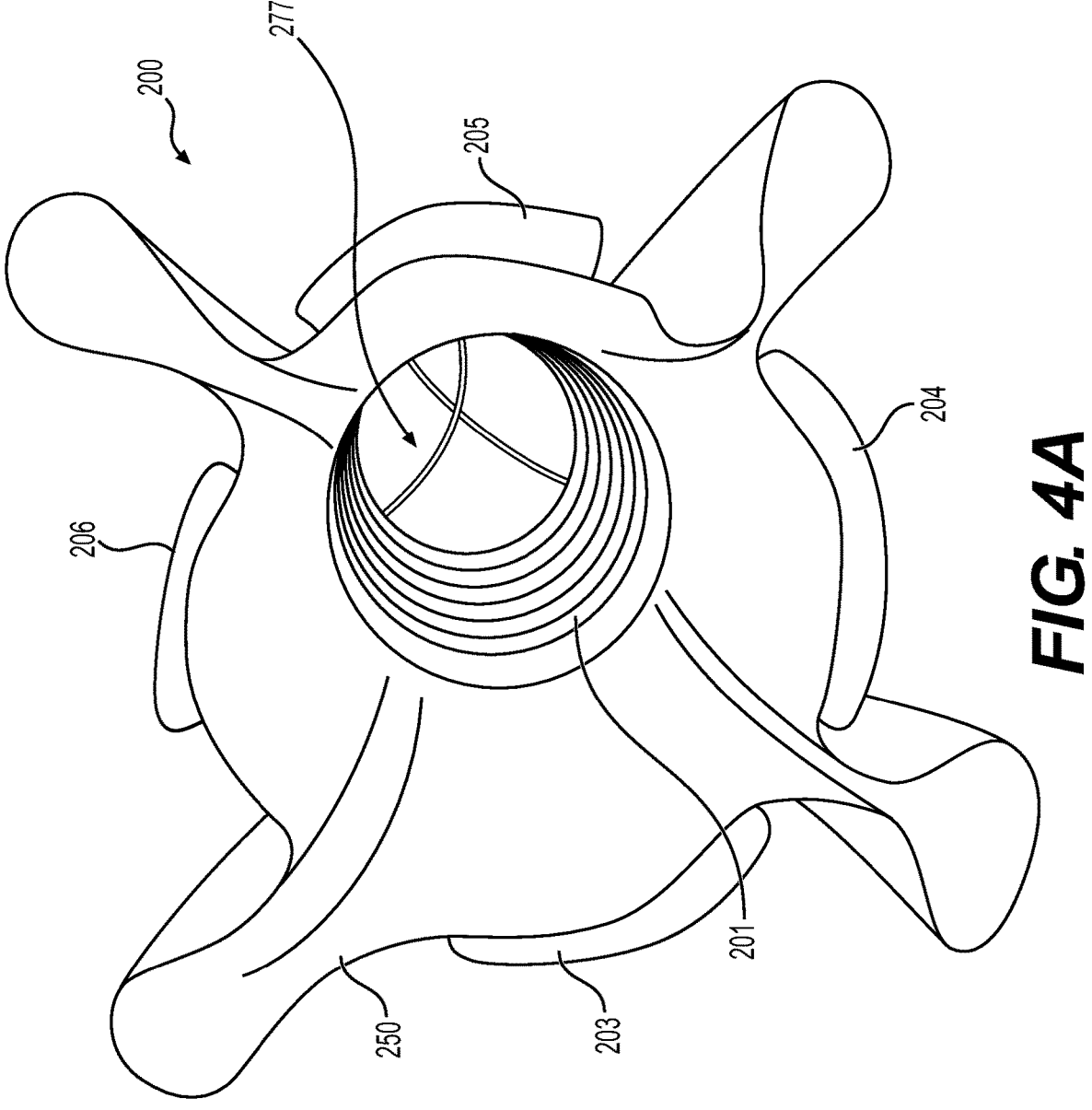
FIGS. 4A-4C are perspective views of a distal portion of the medical device of FIG. 1, according to aspects of this disclosure.

Imaging system 152 may include one or more cameras on endoscope 101 or separate from endoscope 101, and one or more electronic displays of display 154 such as a monitor, television, tablet, phone, or other display device. Cameras or other imaging devices on endoscope 101 may provide images of target anatomy within a body of a patient. For example, a user may visualize a target area using a camera of endoscope 101 at a distal front face of endoscope 101. As shown in FIG. 4A, medical device 200 provides an opening at a distal front face of endoscope 101 when medical device 200 is coupled to endoscope 101, which allows a user to visualize a target area using one or more cameras at a distal front face of endoscope 101.

As shown in FIG. 1, medical device 200 includes a cap 201 and an actuator body 112 extending from cap 201 to a handle assembly 270 at a proximal portion of medical device 200. Actuator body 112 is shown positioned within biopsy port 102 and within shaft 108, however embodiments of this disclosure are not so limited. Actuator body 112 may extend through endoscope 101 to distal tip 110 where cap 201 may be coupled to distal tip 110, or actuator body 112 may extend from cap 201 to handle assembly 270 outside of endoscope 101. Actuator body 112 may be formed by a wire, a coil, a rod, etc.; and/or may include one or more wires, coils, rods, and/or other moveable bodies. Actuator body 112, in some examples, may include one or more wires, coils, rods, etc. movably positioned within a sheath, tube, outer coil, etc.

Articulation section 122 and distal tip 110 of endoscope 101 may be maneuvered while being delivered to the treatment site and/or positioned relative to the treatment site, for example, in a retroflex position. In some aspects, the retroflex position may be used when the treatment site is in the subject's esophagus, stomach, duodenum, colon, or other portion of the gastrointestinal (GI) tract.

Although the treatment site is discussed as being in the patient's GI tract, this disclosure is not so limited, as the treatment site may be any internal lumen or other tissue within the patient. Additionally, although endoscopes are referenced herein, it will be appreciated that the disclosure encompasses any medical devices having a shaft extending from a proximal end to a distal end, such as ureteroscopes, duodenoscopes, gastroscopes, endoscopic ultrasonography ("EUS") scopes, colonoscopes, bronchoscopes, laparoscopes, arthroscopes, cystoscopes, aspiration scopes, sheaths, or catheters.

Figure 2:
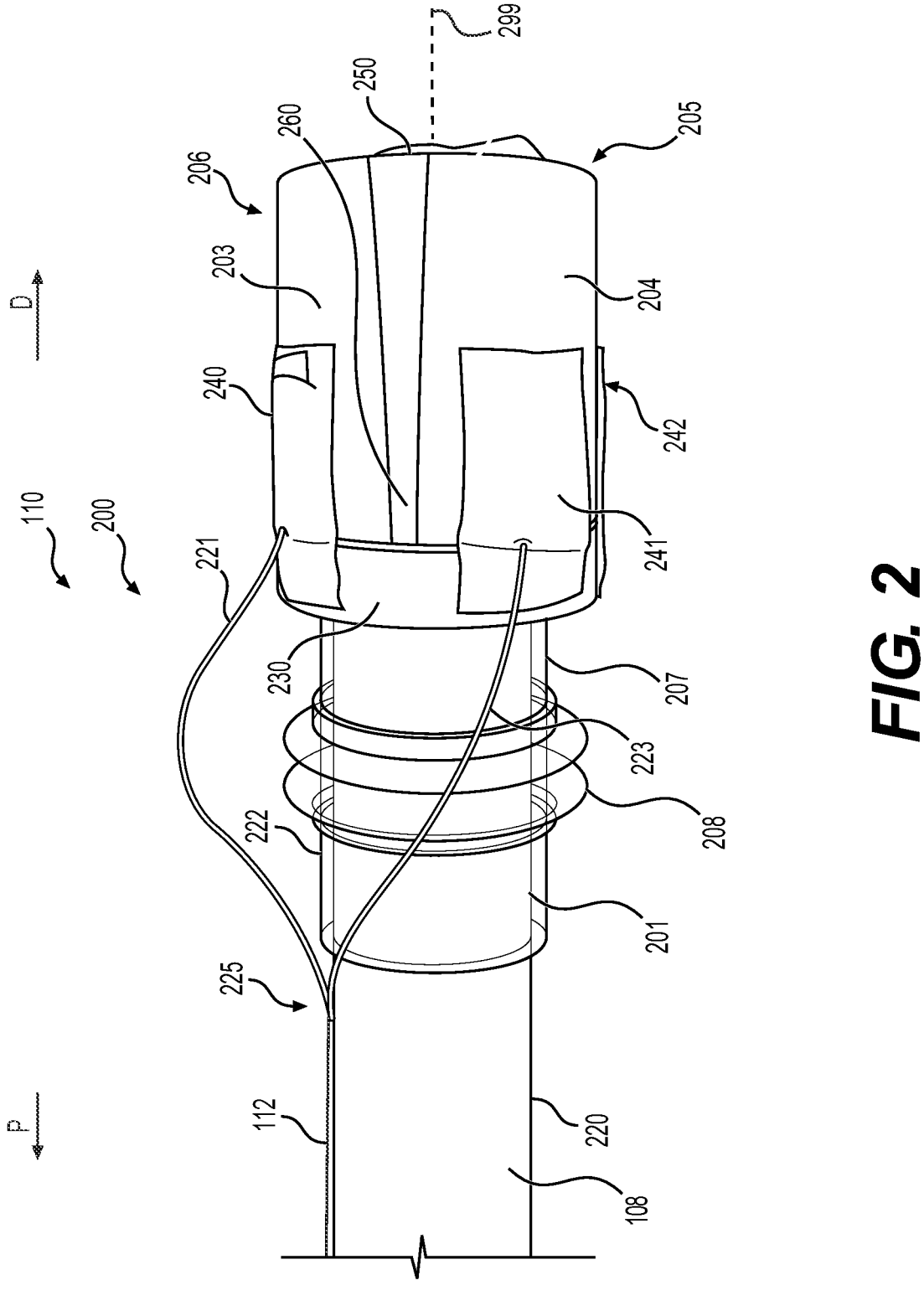
FIG. 2 is a side view of a distal portion of the exemplary medical device and the endoscope of FIG. 1, according to aspects of this disclosure.

FIG. 2 illustrates a side view of a distal portion of medical device 200 coupled to distal end 110 of endoscope 101, with cap 201 coupled to shaft 108. Cap 201 may include a cap body 222 with a lumen 277 (shown in FIG. 4A) extending longitudinally through cap body 222. Cap body 222 may be cylindrical, and may be configured to couple to a radially-outward facing surface 220 of shaft 108, relative to a central longitudinal axis 299 of shaft 108. Cap body 222 may include one or more circular protrusions 208 extending circumferentially about cap body 222 and protruding radially-outward, relative to central longitudinal axis 299. Protrusions 208 may be configured to facilitate positioning and/or coupling of cap 201 to shaft 109, for example by providing increased level of grip to the user and/or a portion of cap 201 for the user to hold while sliding cap 201 onto shaft 108. In some examples, cap body 222 may include radiopaque markings and/or protrusions configured to facilitate visualization of cap 201 (e.g., via X-ray, CT scan, etc. or other external visualization techniques). A distal portion 230 of cap body 222 may protrude radially-outward, relative to axis 299, relative to a proximal portion of cap 201. Distal portion 230 may be coupled to one or more petal bodies 203-206 via one or more hinge assemblies 240-242. In some examples, the one or more petal bodies 203-206 may also be directly coupled to distal portion 230, and may be rotatable relative to distal portion 230. Although only three hinge assemblies 240-242 are shown, there may be on hinge assembly 240-242 per each petal body 203-206, or any other number of hinge assemblies 240-242, such as multiple hinge assemblies 240-242 per petal body 203-206.

Each petal body 203-206 may be substantially rectangular and may be curved such that each petal body 203-206 extends circumferentially about central longitudinal axis 299. Each petal body 203-206 may extend to a distalmost end of medical device 200, and may be substantially the same longitudinal length as each other petal body 203-206. Alternatively, one or more petal bodies 203-206 may be different sizes, for example, when patch 250 is a non-circular or otherwise irregular shape. Petal bodies 203-206 may be biased towards a closed position shown in FIG. 2, in which each petal body 203-206 is substantially parallel to central longitudinal axis 299. Hinge assemblies 240-242 may bias petal bodies 203-206 towards a closed position. Although not shown in FIG. 2, each petal body 203-206 may be biased towards a closed position by a separate hinge assembly 240-242 from each of the other petal bodies 203-206. For example, each hinge assembly 240-242 may include a spring bias towards a closed position of petal bodies 203-206.

As will be discussed in further detail herein in relation to FIGS. 5A and 5B, each petal body 203-206 may include a coupling feature, such as slot 515, configured to couple to patch 250, for example, by receiving a distal portion of patch 250. Although medical device 200 includes four petal bodies 203-206, embodiments of medical device 200 are not so limited and may include 1, 2, 3, 4, 5, 6, 7, 8, or any other suitable number of petal bodies. The longitudinal length of each petal body 203-206 may be scaled up or down dependent on the size of patch 250 coupled to the petal bodies 203-206.

Each petal body 203-206 may be actuatable via a control body 221, 223. As shown in FIG. 2, each control body 221, 223 may be coupled to a respective hinge assembly 240-242, respectively, and extend proximally from the respective hinge assembly 240-242. Although not shown in FIG. 2, one respective control body may be coupled to each petal body 203-206, for example, via a corresponding hinge assembly 240-242. Each control body 221, 223 may be a wire, a flexible shaft, a coil, a rod, etc. and may extend proximally to a joint 225. Each control body 221, 223 may be coupled to actuator body 112 at joint 225. Each control body 221, 223 may have a longitudinal length configured to actuate each respective petal body 203-206 when actuator body 112 is moved (e.g., pulled) proximally. In some examples, each control body 221, 223 may have a longitudinal length configured to actuate each respective petal body 203-206 at the same time as each other petal body 203-206 when actuator body 112 is moved (e.g., pulled) proximally. Control bodies 221, 223 are configured to provide a mechanism for the user to transition petal bodies 203-206 from a closed configuration (shown in FIG. 2) to an open configuration (shown in FIG. 4C). In some examples, a user may partially deploy patch 250 by not fully deploying patch 250 (e.g. by the user stapping actuation of actuator body 112 when petal bodies 203-206 are in a partially open configuration) in order to visualize patch 250 with a camera of endoscope 101 to confirm position of patch 250, and then proceed to fully deploy patch 250 by transitioning to a fully open configuration.

Specifically, each control body 221, 223 may be coupled to each respective petal body 203-206 at a position distal from the hinge about which the petal body 203-206 rotates. When actuator body 112 is moved proximally, each control body 221, 223 is pulled proximally and pulls or otherwise urges each petal body 203-206 proximally, thus rotating each petal body 203-206 relative to cap body 222. For example, via actuation of actuator body 112, each petal body 203-206 may move between a first position (e.g. a closed position) in which each petal body 203-206 is substantially parallel to central longitudinal axis 299, to a second position in which each petal body 203-206 is transverse to central longitudinal axis 299. In some examples, petal bodies 203-206 may transition from the closed position to a fully open position in which each petal body 203-206 is substantially perpendicular to central longitudinal axis 299. In other examples, petal bodies 203-206 may transition from the closed position to a position in which each petal body 203-206 extends proximally as the petal body extends radially-outward, relative to central longitudinal axis 299, from shaft 108. In some examples, each petal body 203-206 may be capable of rotating approximately one hundred and eighty degrees from the closed position to a second position in which (i) each petal body extends in an opposite direction from the closed position and (ii) each petal body is substantially parallel to central longitudinal axis 299.

Each control body 221, 223 may be positioned outside (e.g., radially outward) of shaft 108, and joint 225 may connect each control body 221, 223 to actuator body 112 outside of shaft 108. In other examples, each control body 221, 223 and actuator body 112 may extend within shaft 108 to a proximal portion of device 200, such as through a working channel of shaft 108 to biopsy port 102. In such a configuration, cap body 222 may include one or more lumens configured to allow control bodies 221, 223 to pass through cap 201 and into a working channel of shaft 108. Each control body 221, 223 may be coupled to handle assembly 270 via actuator body 112. Actuation of actuator body 112 will be discussed further herein in relation to FIG. 3.

Patch 250 may be coupled to each petal body 203-206, for example at a distal portion of each petal body 203-206. As shown in FIG. 4A, patch 250 may also be coupled to an interior portion of cap 201, and may extend within lumen 277. For example, a proximal portion 260 of patch 250 may extend around a circular ridge of cap 201 and may be removably coupled to the circular ridge of cap 201.

Patch 250 may be movably coupled to cap 201, and may be configured to radially expand and contract via actuation of petal bodies 203-206. For example, movement of actuator body 112 may extend, retract, or otherwise position patch 250 relative to cap 201. Moreover, in some aspects, movement of actuator body 112 and control bodies 221, 223 may help to release or deploy patch 250 from cap 201, for example, to deliver patch 250 to a treatment site, which may help perform hemostasis. The expansion and contraction of patch 250 relative to cap 201 will be discussed further herein in relation to FIGS. 4A-4C. In some examples, patch 250 may include one or more internal biasing structures, such as wires or coils, to bias patch 250 towards an open configuration or a closed configuration.

Patch 250 may be a biodegradable and/or biocompatible patch of any suitable shape and any suitable dimension, e.g., based on the nature of the target tissue site. Patch 250 may be flexible and may have any shape such as, e.g., approximately square, approximately rectangular, rounded square, rounded rectangle, ovate, circular, among other possible shapes. In some examples, the thickness of the patch 250 may be on the order of millimeters, e.g. ranging from approximately 0.1 mm to approximately 5.0 mm or, more specifically, from approximately 0.7 mm to approximately 2.0 mm. Patch 250 may be sufficiently sized to cover the target tissue with a margin for resection. Thus, patch 250 can come in many sizes to accomplish such a task. In some aspects, patch 250 may be approximately 50 mm by 50 mm (i.e., approximately 2 inches by 2 inches).

Patch 250 may be of any suitable color, including clear. Patch 250 may be formed of any suitable material, e.g., nettings, meshes, cloths, gelatins, or polysaccharides (chitosan, cellulose, starch, alginates, etc.) that may be further modified with synthetic biocompatible materials (pHEMA, PGA, PLA, PCA, PEG, etc.). In some aspects, patch 250 may be formed of a bioadhesive material, for example, such as chitosan, modified chitosan, cellulose, pHEMA, PVA, PEG, or composites of one or more of these polymers.

Additionally, for example, patch 250 may be comprised of polypropylene, polyester, Polytetrafluoroethylene (PTFE), expanded Polytetrafluoroethylene (ePTFE), and/or silicone. Patch 250 may be adhered to the target tissue using materials commonly known in the art, such as, for example, fibrin glue, hydrogel, and/or cyanoacrylate. Alternatively or additionally, patch 250 may be comprised of and/or dosed with agents to prevent the shedding of cells from the target tissue or to treat the target site. In some aspects, patch 250 may include a treatment agent, for example, an antibiotic and/or hemostatic agent. Moreover, after patch 250 is delivered to the treatment site, the user may spray, apply, or otherwise deliver one or more hemostatic agents (e.g., one or more hemostatic powders), for example, through a working channel of endoscope 101 or another medical device.

Figure 3:
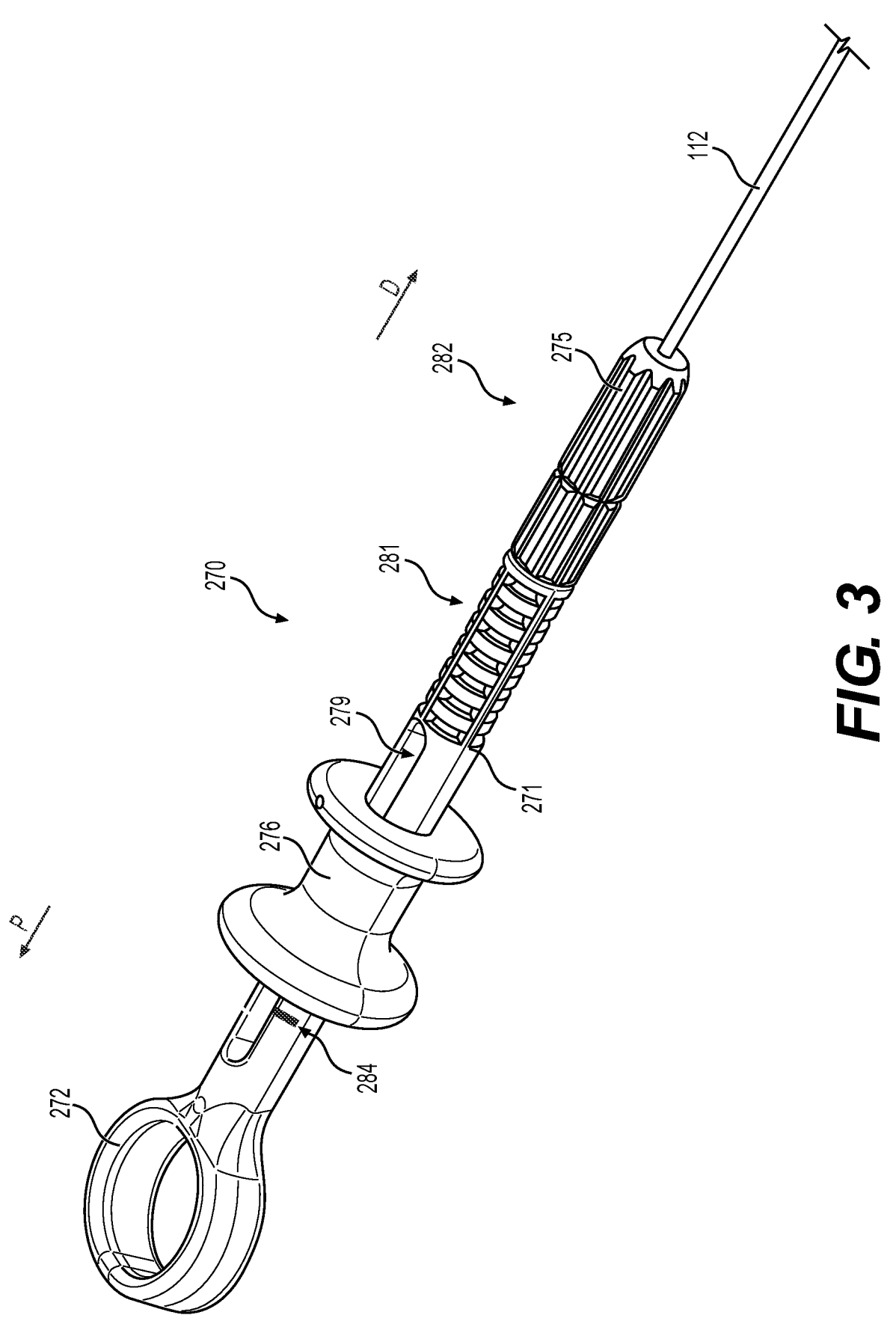
FIG. 3 is a perspective view of a proximal portion of the medical device of FIG. 1, according to aspects of this disclosure.

FIG. 3 illustrates a perspective view of handle assembly 270 of medical device 200. Handle assembly 270 may include a main body 271 and a moveable body 276. Main body 271 may be generally cylindrical and may include a ring portion 272 at a proximalmost end of main body 271. Ring portion 272 may be configured to receive one or more of a user's fingers to facilitate holding handle assembly 270. Main body 271 may include ridged portions 281 configured to facilitate gripping main body 271, and a slot 279 may extend longitudinally through main body 271. Slot 279 may be configured to receive a portion of moveable body 276. A distal end portion 282 of main body 271 may include a cylindrical coupler 275, and coupler 275 may couple actuator body 112 to main body 271. Actuator body 112 may be configured to move proximally and distally through coupler 275. Coupler 275 may be coupled to a portion of the endoscope handle, and/or a sheath (not shown) may surround actuator body 112 and be coupled to main body 271, such that movement of movable body 276 controls the movement of actuator body 112 relative to endoscope 101 and/or the sheath. Moveable body 276 may include two radially extending portions at each of a proximal end and a distal end of moveable body 276, with an indented portion connected the two radially extending portions.

A lumen may extend through main body 271 to allow actuator body 112 to be positioned within main body 271 and move within main body 271. A proximal end of actuator body 112 may be coupled to moveable body 276, and proximal or distal movement of moveable body 276 longitudinally relative to main body 271 may move actuator body 112 proximally or distally, respectively. In some examples, sliding moveable body 276 proximally relative to main body 271 may be configured to transition petal bodies 203-206 from a closed configuration to an open configuration, and release of moveable body 276 by a user may transition petal bodies 203-206 from an open configuration to a closed configuration, for example, via one or more biasing members (e.g., hinge assemblies 240, 241). Moveable body 276 may be cylindrical, may be hour-glass shaped, and may be configured to receive one or more fingers to facilitate movement of moveable body 276 relative to main body 271.

Handle assembly 270 may also include one or more marking and/or projections 284. For example, one marking and/or projection 284 may indicate to a user when petal bodies 203-206 have reached a position that will deploy patch 250. In some examples, projection 284 may interact with moveable body 276 (e.g., a ridge that may require additional proximal force on movable body 276 to overcome) and/or provide an audible click when petal bodies 203-206 have reached a position that will deploy patch 250. In other examples, marking 284 may signal or otherwise indicate to a user that petal bodies 203-206 have reached a position that will deploy patch 250 when moveable body 276 is aligned with marking 284. In some examples, although not shown, moveable body 276 may include a recess portion configured to receive projection 284, for example, such that projection 284 snaps or otherwise fits into the recess portion when movable body 276 is in a position on main body 271 such that petal bodies 203-206 have reached a position that will deploy patch 250.

Figure 4B:
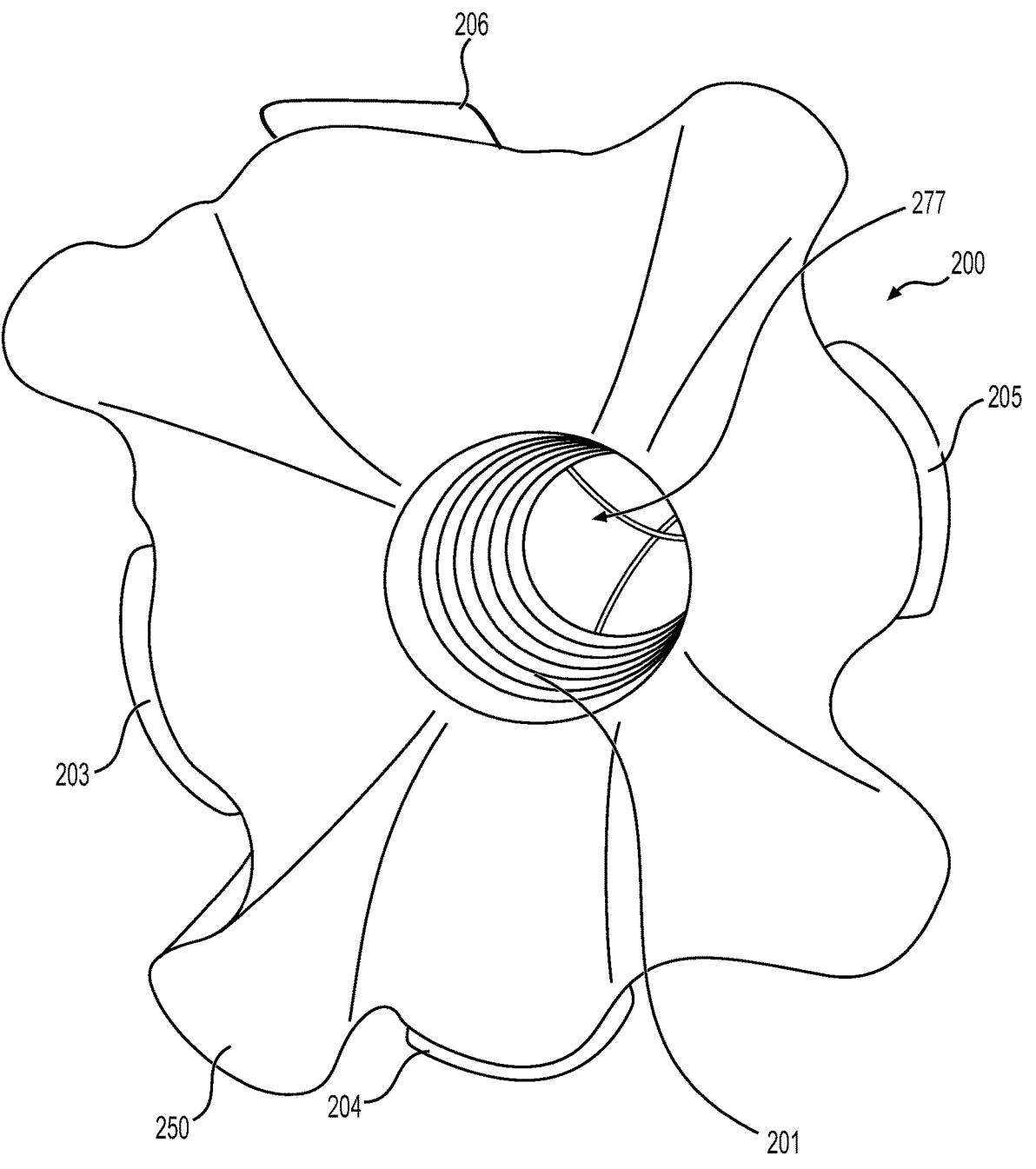
Figure 4C:
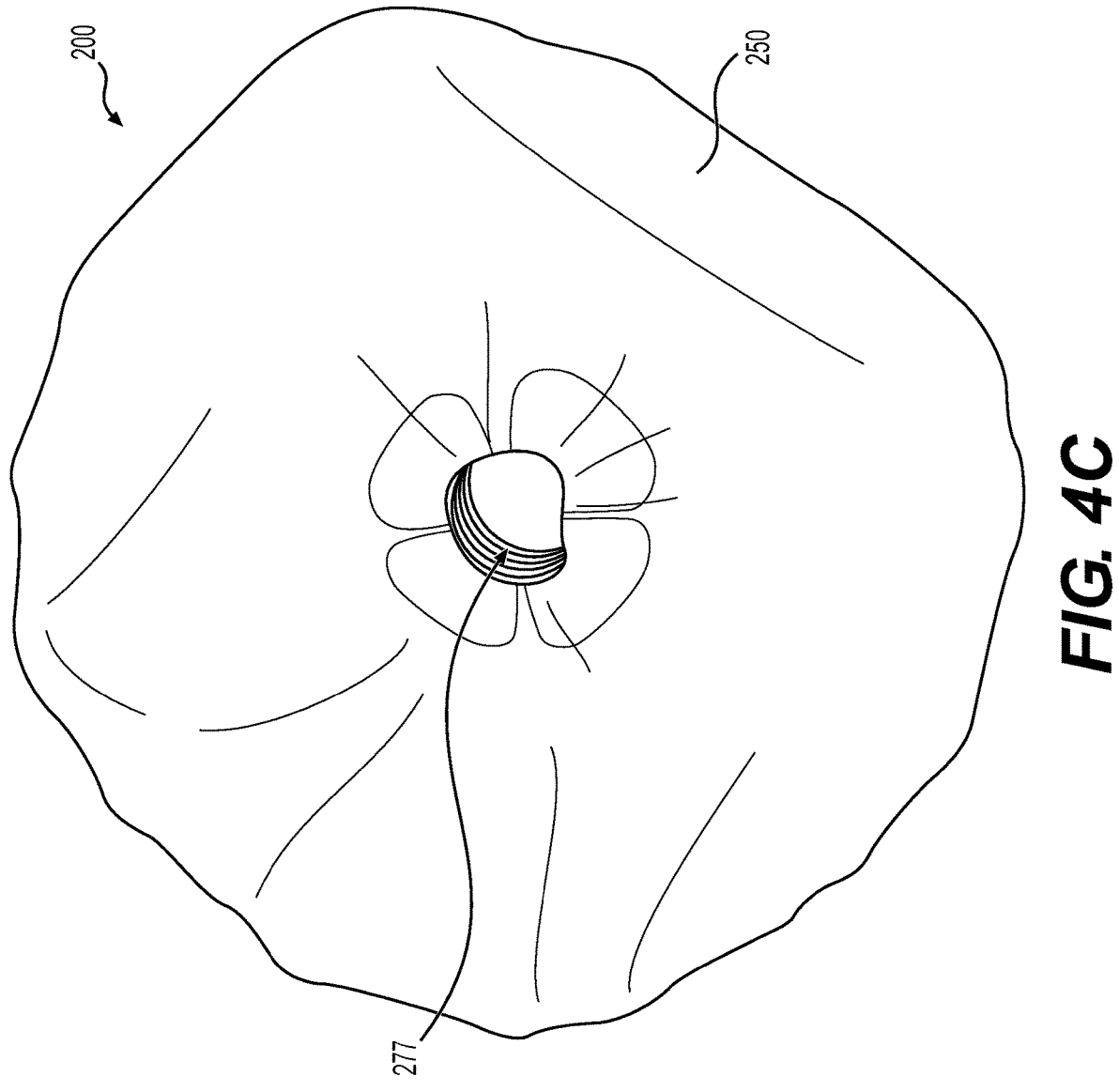

FIGS. 4A-4C illustrate perspective views of medical device 200 during the steps to deploy patch 250 from cap 201. FIG. 4A illustrates patch 250 and cap 201, including petal bodies 203-206 when a user has started to actuate moveable body 276 by moving moveable body 276 proximally relative to main body 271 (FIG. 3), thus moving actuator body 112 proximally to pull control bodies 221, 223 proximally. This proximal movement of control bodies 221, 223 causes petal bodies 203-206 to rotate about hinge assemblies 240-242 (FIG. 2), and thus the distal ends of each petal body 203-206 start to move radially outward, relative to central longitudinal axis 299 (FIG. 3), and away from each other. Since patch 250 is coupled to distal end portions 512 (shown in FIGS. 5A and 5B) of each petal body 203-206, and also coupled to cap 201 at a proximal end of patch 250, patch 250 starts to transition from a folded configuration, when medical device 200 is in a closed configuration, to an open configuration. As shown in FIG. 4A, patch 250 is starting to be spread out or unfolded by the movement of petal bodies 203-206. FIG. 4B illustrates patch 250 in a nearly unfolded configuration, with petal bodies 203-206 continuing to move radially outward compared to FIG. 4A. FIG. 4C illustrates medical device 200 in a fully open configuration with patch 250 completely unfolded and released from cap 201. The relative movement of moveable body 276 relative to main body 271 on handle assembly 270 controls the position of petal bodies 203-206.

When a user moves moveable body 276 proximally to the point of release of patch 250, for example to position movable body 276 at marker 284, patch 250 may slide off of each petal body 203-206 and pop out from cap 201 due to the forces applied by each petal body 203-206 on patch 250. Thus, a user may selectively actuate medical device 200 to position patch 250 at a target area and deploy patch 250 from cap 201. In some examples, a user may utilize a camera of endoscope 101 (e.g., coupled to one or more of controller 151, imaging system 152, power supply 153, and/or display 154 via umbilicus 105) to visualize a target area (e.g. treatment site) within a body of a patient, and then release patch 250 at the target area by actuating moveable body 276.

Figure 5A:
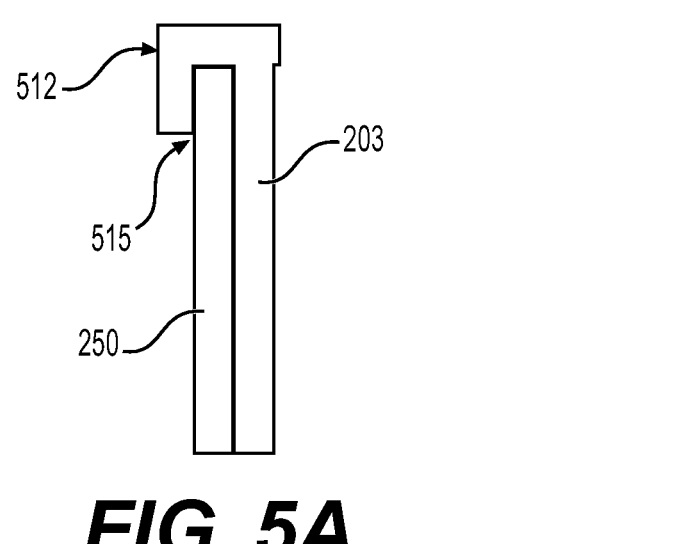
FIGS. 5A and 5B are side views, respectively, of a portion of the medical device of FIG. 1, according to aspects of this disclosure.
Figure 5B:
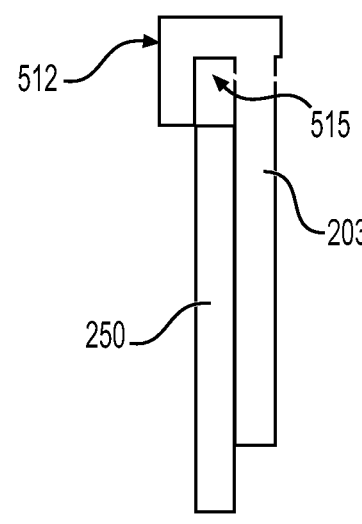

FIGS. 5A and 5B illustrate distal end portions 512 of petal body 203. Each of petal bodies 203-206 may include a distal end portion 512. Distal end portion 512 may be substantially U-shaped and may include a slot or recess portion 515 configured to receive a portion (e.g., a distal portion) of patch 250. Patch 250 may slide into recess portion 515 to temporarily couple patch 250 to distal end portion 512. By coupling patch 250 to distal end portion 512 of each petal body 203-206, petal bodies 203-206 may fold and unfold patch 250 by pivoting about each hinge assembly 240-242. A distal portion of patch 250 may slide out of recess portion 515 when petal bodies 203-206 are positioned at or beyond a certain position (e.g., corresponding to the position of the moveable body 276 at the protrusion/marking 284). Recess portion 515 may be configured to receive patch 250 and may have a width of 0.35 mm-2.5 mm, or any other width suitable to couple patch 250 to distal end portion 512.

Figure 6:
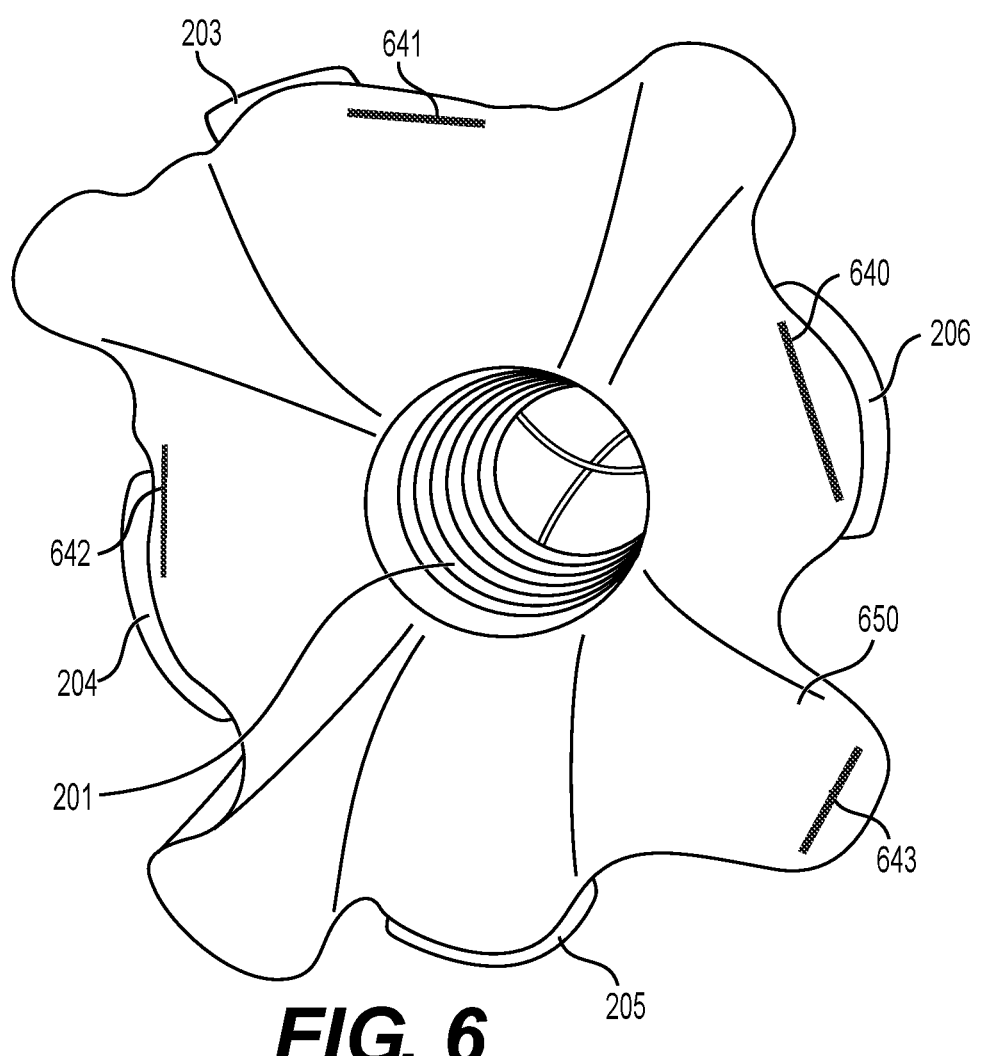
FIG. 6 is a distal portion of an alternative embodiment of a medical device, according to aspects of this disclosure.

FIG. 6 illustrates a distal portion of medical device 200 (e.g., end cap 201) with an alternative embodiment of patch 650. FIG. 6 illustrates end cap 201, including petal bodies 203-206, and patch 650 in a partially deployed configuration. Patch 650 may have any of the attributes of patch 250 described herein. Additionally, patch 650 may include one or more hooks or series of hooks 640-643 positioned about one or more portions of a perimeter portion of patch 650. Hooks 640-643 may be fixedly coupled to patch 650, and may be configured to help facilitate coupling patch 650 to tissue of a patient, for example, at the treatment site. In some examples, hooks 640-643 may each be curved towards a central portion of patch 650.

During operation, a user may first couple medical device 200 to an insertion device, such as endoscope 101. The user may then maneuver endoscope 101, using one or more imaging devices, illumination devices, etc. (not shown) at distal tip 110, to navigate to a treatment site with a body of a patient. The user may, while visualizing the treatment site, then actuate moveable body 276 by translating moveable member 276 proximally to transition petal bodies 203-206 from a closed configuration to an open configuration, and then deploy patch 250 at the treatment site. When the user releases moveable body 276, petal bodies 203-206 may transition from an open configuration to a closed configuration due to the bias provided from hinge assemblies 240-242.

Once patch 250 is deployed and delivered to the treatment site, the user may inspect patch 250 and the treatment site, for example, using one or more imaging devices, illumination devices, etc. of endoscope 101. The user may reposition patch 250, for example, using one or more auxiliary medical devices, such as a grasper or other auxiliary medical device (e.g., delivered to the treatment site through a working channel of endoscope 101). Moreover, the user may apply a hemostatic agent (e.g., a hemostatic powder) to the delivered patch 250, for example, via one or more auxiliary medical devices delivered through a working channel of endoscope 101.

Various aspects of medical system 100, for example, medical device 200 with patch 250, cap 201, and handle assembly 270, may have a low cost and may be disposable (i.e., a single use device). Medical device 200 may be coupled to any type of scope to help deliver one or more patches 250 to a treatment site (e.g., endoscopically), and coupling cap 201 to the distal end of a scope may be quick and user-friendly. The patch 250 may be positioned at least partially within cap 201 and may be coupled to petal bodies 203-206. Petal bodies 203-206 may also cover patch 250 when in a closed configuration to help to protect patches 250 from fluids, tissues, materials, etc. during the delivery of endoscope 101 to the treatment site.

Additionally, medical device 200 may allow for one or more patches 250 to be delivered to a treatment site in a minimally invasive procedure (e.g., endoscopically), without having to deliver the one or more patches 250 through a working channel of endoscope 101. In this aspect, the one or more patches 250 may be larger than patches passed through the working channel. Moreover, the one or more patches 250 may not interfere with the delivery of one or more auxiliary medical device, delivery of fluid, application of suction, etc., which may be done through the working channel.

Furthermore, in some aspects, patch 250 may be positioned and repositioned before being deployed. For example, as discussed, the user may manipulate movable body 276 relative to main body 271 to position and reposition patch 250 via movement of actuator body 112. This positioning and repositioning may be done under direct visualization, for example, via one or more cameras of endoscope 101. As patch 250 is coupled to endoscope 101 via cap 201, a distal end face of endoscope 101 may be substantially unobstructed and allow for visualization of anatomy via a camera on distal end face of endoscope 101. Additionally, in some aspects, the user may lock or otherwise secure the position of movable body 276 relative to main body 271, via a locking mechanism, such as protrusion 284 moving into a recess of moveable body 276.

The positioning and deployment of patch 250 (e.g., via movable body 276 and actuator body 112) may be straightforward and user-friendly, which may allow the user to be a surgical technician, while the physician performs one or more other tasks during the procedure.

While principles of this disclosure are described herein with the reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A medical device, comprising:
a handle, wherein the handle includes a movable body and a main body;
a cap configured to be coupled to a distal end of a scope;
a patch, wherein the patch is moveable relative to the cap; and
a petal body, wherein the patch is removably coupled to the petal body;
an actuator body coupling the patch to the moveable body such that movement of the moveable body extends the patch from the cap, and
wherein the petal body is configured to transition between a closed configuration in which the patch is retracted, and an open configuration in which the patch is extended radially-outward from a central longitudinal axis of the scope.

2. The medical device of claim 1, wherein the petal body is a plurality of petal bodies, and the patch is removably coupled to each of the plurality of petal bodies.

3. The medical device of claim 2, wherein the actuator body includes a plurality of control bodies, and each of the control bodies are coupled to a separate petal body.

4. The medical device of claim 3, wherein each of the control bodies are coupled together at a joint proximal to the cap and extend distally from the joint, and wherein the actuator body further includes a first actuator body extending proximally from the joint.

5. The medical device of claim 2, wherein each of the plurality of petal bodies are positioned circumferentially about a distal portion of the cap.

6. The medical device of claim 1, wherein the cap includes a ridge configured to couple to the patch.

7. The medical device of claim 1, wherein the petal body is coupled to the cap via a hinge assembly.

8. The medical device of claim 7, wherein the petal body is configured to pivot relative to the cap when the moveable body is translated proximally.

9. The medical device of claim 7, wherein the hinge assembly is configured to bias the petal body towards the closed configuration.

10. The medical device of claim 1, wherein the petal body includes a slot at a distal portion of the petal body, and wherein the slot receives a portion of the patch.

11. The medical device of claim 1, wherein the patch includes a plurality of adhesion members positioned about at least a portion of a perimeter of the patch.

12. The medical device of claim 1, wherein the actuator body extends through the main body and is coupled to the moveable body.

13. The medical device of claim 1, wherein the cap includes a protrusion extending circumferentially about the cap.

14. The medical device of claim 1, wherein the movable body of the handle is movable within a slot in the main body of the handle.

15. The medical device of claim 1, wherein the patch includes a hemostatic agent.

\* \* \* \* \*